United States Patent
Nikic et al.

(10) Patent No.: US 10,330,720 B2
(45) Date of Patent: *Jun. 25, 2019

(54) SYSTEMS AND METHODS FOR PROPAGATING BRUSH DISCHARGE TESTING

(71) Applicant: The Boeing Company, Chicago, IL (US)

(72) Inventors: Dejan Nikic, Seattle, WA (US); Arthur C. Day, Seattle, WA (US)

(73) Assignee: The Boeing Company, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/152,715

(22) Filed: Oct. 5, 2018

(65) Prior Publication Data

US 2019/0041449 A1 Feb. 7, 2019

Related U.S. Application Data

(63) Continuation of application No. 15/414,483, filed on Jan. 24, 2017, now Pat. No. 10,120,014.

(51) Int. Cl.
*G01R 31/12* (2006.01)
*G01N 27/60* (2006.01)
(Continued)

(52) U.S. Cl.
CPC ......... *G01R 31/1218* (2013.01); *G01N 27/60* (2013.01); *G01N 27/61* (2013.01);
(Continued)

(58) Field of Classification Search
CPC .... G01R 31/00; G01R 31/12; G01R 31/1218; G01R 31/1272; G01R 31/16;
(Continued)

(56) References Cited

U.S. PATENT DOCUMENTS 3,928,034 A * 12/1975 Regensburger ...... G03G 5/0436
430/58.05
3,960,555 A * 6/1976 Goffe ........................ G03G 5/04
430/41

(Continued)

OTHER PUBLICATIONS

Blythe et al., Characteristics of Propagating Electrostatic Discharges on Dielectric Films, Journal of Electrostatics, vol. 10, pp. 321-326, 1981.

(Continued)

*Primary Examiner* — Hoai-An D. Nguyen
(74) *Attorney, Agent, or Firm* — Dascenzo Intellectual Property Law, P.C.

(57) ABSTRACT

Propagating brush discharge testing systems include an initiation electrode, a high-voltage switch, a sensor, and a controller. The initiation electrode has an exposed tip positioned adjacent to a surface of a test article. The high-voltage switch is configured to selectively isolate the initiation electrode from ground potential. The sensor is positioned and configured to detect a propagating brush discharge between the initiation electrode and the test article. The controller is programmed to operate the high-voltage switch to ground the initiation electrode.

20 Claims, 2 Drawing Sheets

(51) Int. Cl.
*G01R 31/16* (2006.01)
*G01N 27/61* (2006.01)
*G01R 29/24* (2006.01)
*G01R 15/16* (2006.01)

(52) U.S. Cl.
CPC ............ *G01R 31/16* (2013.01); *G01R 15/165* (2013.01); *G01R 29/24* (2013.01)

(58) Field of Classification Search
CPC .. G01R 31/31901; G01R 29/00; G01R 29/08; G01R 29/0842; G01R 29/12; G01R 29/24; G01R 19/00; G01R 19/0023; G01R 15/00; G01R 15/14; G01R 15/16; G01R 15/165; G01R 5/00; G01R 5/28; G01R 27/2617; G01R 27/00; G01R 27/60; G01R 27/61
USPC .... 324/452, 456, 457, 76.11, 109, 500, 512, 324/536, 537, 551, 554, 555, 557, 72, 324/72.5
See application file for complete search history.

(56) References Cited

U.S. PATENT DOCUMENTS

| | | |
|---|---|---|
| 4,096,013 A | 6/1978 | Lutzmann et al. |
| 4,875,060 A | 10/1989 | Masuda et al. |
| 6,541,988 B2 | 4/2003 | Dangelmayer et al. |
| 7,795,878 B2 | 9/2010 | Purdy et al. |
| 8,439,560 B1 | 5/2013 | Ladd |
| 10,120,014 B2 * | 11/2018 | Nikic ..................... G01N 27/60 |
| 2005/0258842 A1 | 11/2005 | Maloney |
| 2014/0017821 A1 | 1/2014 | Fenouillet-Beranger et al. |

OTHER PUBLICATIONS

Abstract of: Dahn et al., "Propagating brush discharge initiation of dust layers—A new test method," *Journal de Physique* (Aug. 2002), vol. 12, No. 7, pp. 65-69. Abstract downloaded from jp4.journaldephysique.org/articles/jp4/abs/2002/07/jp4Pr7p65/jp4Pr7p65.html.

DEKRA Insight, "Propagating Brush Discharge Testing and Breakdown Voltage Measurement," downloaded from dekra-insight.com/en/topic/propagating-brush-discharge-testing-and-breakdown-voltage-measurement, published at least as early as Oct. 13, 2016.

Yamaguma et al., "Observation of Propagating Brush Discharge on Insulating Film With Grounded Antistatic Materials," *IEEE Transactions on Industry Applications* (Mar./Apr. 2004), vol. 40, No. 2, pp. 451-456.

* cited by examiner

SYSTEMS AND METHODS FOR PROPAGATING BRUSH DISCHARGE TESTING

RELATED APPLICATION

This application is a continuation of and claims priority under 35 U.S.C. § 120 to U.S. patent application Ser. No. 15/414,483, which is entitled "SYSTEMS AND METHODS FOR PROPAGATING BRUSH DISCHARGE TESTING," which was filed on Jan. 24, 2017, which issued as U.S. Pat. No. 10,120,014 on Nov. 6, 2018, and the disclosure of which is hereby incorporated by reference.

FIELD

The present disclosure relates to systems and methods for propagating brush discharge testing.

BACKGROUND

Electrostatic charge accumulation may lead to electrostatic discharge which may present a hazard in many situations. Electrostatic discharge may cause ignition of flammable substances. Unlike other potential ignition sources, electrostatic charge accumulation may be due to normal operations. For example, liquid fuel flow through a tube may generate electrical charge in the fuel and/or tube that accumulates because the fuel and/or tube are electrically insulating. Additionally, in fuel handling, transport, and storage, liquid fuel may form a vapor or aerosol in use. If exposed to oxygen and a sufficiently intense electrostatic discharge under uncontrolled conditions, the fuel may ignite unexpectedly.

Prevention and characterization of electrostatic discharge may be important to industries which use or produce flammable environments. Industrial examples include fuel production, fuel transportation, vehicle operation, mining operations, chemical processing, metal fabrication, power plant construction and operation, and operations which involve combustible particulate such as sawdust, metal, flour, and grain.

Propagating brush discharges, one of many types of electrostatic discharges, are known to be incendive in many situations. A propagating brush discharge is a type of electrostatic discharge that occurs on a dielectric surface (also called an insulating surface). If a dielectric surface is sufficiently insulating and has a sufficiently high dielectric strength (breakdown field strength), opposite electrical charge can accumulate in layers on opposite sides of the surface. Generally, this bi-layer of opposite charge accumulation occurs when the dielectric layer has one side in contact with a source of mobile charge carriers (typically a grounded metal surface) and the other side is exposed to a charge source (e.g., friction due to material flow). Such an arrangement may allow the exposed side of the dielectric layer to accumulate a large charge density (e.g., 0.1-10 $mC/m^2$ (millicoulombs per square meter)). A propagating brush discharge occurs when the formerly isolated sides of the dielectric layer become electrically connected. Electrical connection between the two sides of the dielectric layer may be formed by a point in the dielectric layer that experiences dielectric breakdown, by flashover on the surface to an exposed portion of the source of mobile charge carriers, or by mechanical contact with a grounded component (or other source of mobile charge carriers). The discharge forms a radiating branch pattern (a radial Lichtenberg form) that drains some or all of the charge from the surfaces.

Propagating brush discharges typically arise when the electrical potential between the opposite sides of the dielectric layer is several thousand volts (e.g., greater than 4 kV (kilovolts)), the dielectric layer is thin (e.g., less than 10 mm (millimeters)), and the accumulated charge density is relatively large (e.g., greater than $0.1\ mC/m^2$). The total energy released by a propagating brush discharge may be greater than 1 mJ (millijoules), may occur in less than 10 μs (microseconds), and may have a peak current of greater than 10 A (amperes). Charge accumulation that may lead to propagating brush discharges typically involves rapid mechanical flow of insulating powders or liquids through insulating conduits or conduits including an insulating internal surface, or exposure to high electric fields.

In traditional propagating brush discharge testing, a dielectric layer is charged to produce a bi-layer of static electrical charge on opposing surfaces and a propagating brush discharge is prompted by moving a grounded electrode towards the dielectric layer. The grounded electrode typically has a large bulbous tip and is moved by a person using a long handle. As the grounded electrode is brought close enough to the dielectric layer, the electrical conditions may be sufficient to trigger a propagating brush discharge. The time of initiating a propagating brush discharge is variable and reliant on particular conditions of the test. For example, the approach speed of the grounded electrode, the electrode shape, the electrode position relative to the dielectric layer, the material of the dielectric layer, the voltage of the charged surfaces, and the environmental conditions (e.g., air pressure, humidity, etc.) may affect the precise point in time when a propagating brush discharge may be triggered.

SUMMARY

Systems and methods for performing propagating brush discharge tests are disclosed.

Some systems comprise a grounded layer, a dielectric layer, an initiation electrode, a high-voltage switch, a sensor, and a controller. The dielectric layer has a first surface and is backed by the grounded layer opposite the first surface of the dielectric layer. The initiation electrode has a conductive element that has a body and an exposed tip. The exposed tip is positioned adjacent to the first surface of the dielectric layer such that a voltage differential between the exposed tip and the first surface is sufficient to cause an electrical contact between the exposed tip and the first surface. The body of the conductive element is electrically isolated from the dielectric layer. The high-voltage switch is connected to the initiation electrode and configured to selectively isolate the conductive element of the initiation electrode from ground potential. The sensor is positioned and configured to detect a propagating brush discharge centered at the exposed tip of the initiation electrode. The controller is programmed to operate the high-voltage switch to electrically ground the initiation electrode.

Some systems comprise an initiation electrode, a high-voltage switch, an optical sensor, and a controller. The initiation electrode has a conductive element and an insulating sheath along a body of the conductive element. The conductive element has an exposed tip configured to be positioned adjacent to a test article. The high-voltage switch is connected to the initiation electrode and configured to selectively isolate the conductive element from ground potential. The optical sensor is positioned and configured to sense light generated at the test article due to a propagating brush discharge centered at the exposed tip of the conductive element. The controller is configured to operate the high-voltage switch and the optical sensor to obtain image data of the propagating brush discharge.

DESCRIPTION

Figure 1:
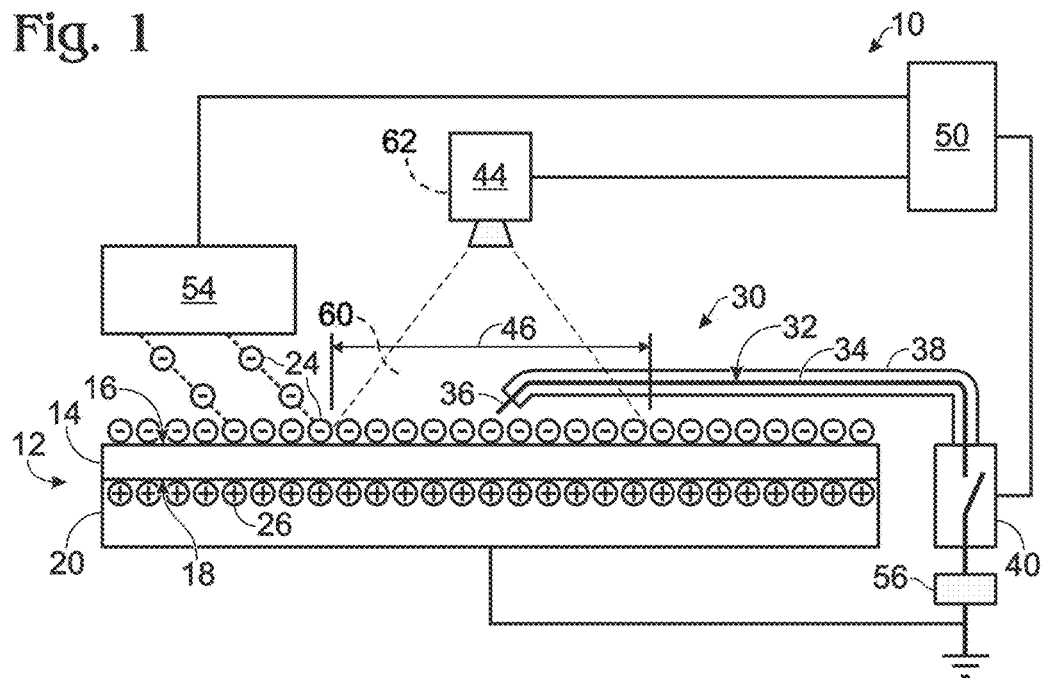
FIG. 1 is a schematic representation of a system for performing a propagating brush discharge test according to the present disclosure.

FIGS. 1-4 illustrate propagating brush discharge testing systems and methods, and propagating brush discharge characteristics. In general, in the drawings, optional and alternative elements may be included. Individual elements illustrated may be omitted from a particular embodiment without departing from the scope of the present disclosure. All elements may not be labelled or shown in each of the figures, but reference numerals associated therewith may be used for consistency.

Systems and methods of propagating brush discharge testing according to the present disclosure are improvements over traditional systems and methods. As an example, systems and methods of the present disclosure do not move an initiation electrode to a charged surface to initiate a propagating brush discharge. As disclosed further herein, an initiation electrode is adjacent to a surface of a dielectric layer and is electrically isolated selectively from ground potential (or other source of mobile charge carriers). The surface may be charged while the initiation electrode is isolated from ground potential. Once the surface is sufficiently charged, a propagating brush discharge may be triggered by grounding the initiation electrode while the initiation electrode is adjacent to the charged surface (or generally by electrically connecting the initiation electrode to the source of mobile charge carriers while the initiation electrode is adjacent to the charged surface). By grounding the initiation electrode while the initiation electrode is at the charged surface, the period of time in which the propagating brush discharge occurs (if any does occur) is substantially defined by the time when grounding (or electrical connection) is performed and not by the various parameters (e.g., approach speed) that introduce variability in the traditional propagating brush discharge testing. Systems and methods of the present disclosure may be used to initiate a propagating brush discharge within a defined time period that is reliably less than 100 ms (milliseconds) or shorter intervals.

FIG. 1 is a schematic representation of a system 10 for performing a propagating brush discharge test. The system 10 includes a test article 12 that has a dielectric layer 14 (also called an insulating layer). The dielectric layer 14 is electrically insulating and may be sufficiently insulative to accumulate a bi-layer of opposite charges that may lead to a propagating brush discharge. The dielectric layer 14 may accumulate charge on a first surface 16 (also called an exposed surface or a test surface) and a second surface 18 (also called a back surface or a covered surface). The first surface 16 of the dielectric layer 14 is substantially exposed to test conditions and configured to receive electrical charge. The system 10 is configured to produce conditions which could result in a propagating brush discharge at the first surface 16 of the dielectric layer 14.

The second surface 18 of the dielectric layer 14 is in electrical and mechanical contact with a grounded layer 20. The grounded layer 20 backs the dielectric layer 14, leaving the first surface 16 exposed. The grounded layer 20 and the dielectric layer 14 may be part, or the whole, of the test article 12. Alternatively, the test article 12 may not include the grounded layer 20. The grounded layer 20 may be applied to the dielectric layer 14 of the test article 12 to form the system 10. A source of mobile charge carriers, whether grounded or not, may serve as the grounded layer 20.

The grounded layer 20 is electrically conductive and connected to electrical ground. The grounded layer 20 has an electrical potential that is substantially ground potential, commonly referenced as zero volts (0 V). The grounded layer 20 typically is metallic and/or an electrical conductor (e.g., a highly conductive metal layer of copper). The grounded layer 20 may readily source or drain electrical charges. While the first surface 16 accumulates electrical charges (in the form of charge particles 24), the electrostatic field of the charge on the first surface 16 polarizes the grounded layer 20 such that opposite charges (mirror charge, in the form of charge particles 26) accumulate at the boundary of the grounded layer 20 and the second surface 18.

Charge particles 24 and charge particles 26 are elementary charge carriers and may be virtual or real particles. For example, charge particles 24 and charge particles 26 each independently may be electrons, negative ions, positive ions, holes, and/or image charges. Charge particles 24 have the opposite electrical polarity as charge particles 26. If one is positively charged, the other is negatively charged. Though FIG. 1 illustrates negative charge particles 24 at the first surface 16 and positive charge particles 26 at the second surface 18, the charge at the first surface 16 may be positive and the charge at the second surface 18 may be negative.

The dielectric layer 14 is configured such that a propagating brush discharge may occur. However, as the test article 12 and the dielectric layer 14 may be tested for attenuation and/or prevention of propagating brush discharges, the dielectric layer 14 may have one or more properties that reduce the occurrence and/or intensity of propagating brush discharges. Generally, the dielectric layer 14 is relatively thin to promote a bi-layer of accumulated charge (i.e., charge particles 24 on first surface 16 and charge particles 26 on second surface 18). The dielectric layer 14 may have a thickness between the first surface 16 and the second surface 18 of at most 10 mm, at most 3 mm, or at most 1 mm, and generally at least 0.001 mm. Generally, the dielectric layer 14 has a dielectric strength (breakdown field strength) that is sufficient to support a high voltage suitable for a propagating brush discharge. Typical test voltages between the first surface 16 and the second surface 18 include at least 4 kV, at least 8 kV, or at least 16 kV, and generally at most 100 kV. Hence, an example of a dielectric layer 14 that is configured to support a 10 kV potential difference across a 1 mm thickness would have a dielectric strength of greater than 10 kV/mm (kilovolts per millimeter). As another example, a dielectric layer 14 that has a dielectric strength of 10 kV/mm would need to have a thickness of greater than 1 mm in order to support a 10 kV potential across the thickness. Many common thermoplastic polymers have a dielectric strength of about 10-30 kV/mm.

High dielectric strength materials may have a dielectric strength that is greater than 50 kV/mm.

In testing, the first surface 16 of the dielectric layer 14 is charged by applying electrical charge to the first surface 16 to achieve a high voltage suitable for a propagating brush discharge. Suitable magnitudes of voltages of the first surface 16 relative to ground potential (which is also the electrical potential of the grounded layer 20) include at least 4 kV, at least 8 kV, or at least 16 kV, and generally at most 100 kV. The first surface 16 may have a positive or a negative voltage relative to ground potential. Charge may be applied to the first surface 16 by a charge source 54 (which may be positioned, designed, and/or configured to charge the first surface 16). The charge source 54 may include and/or may be a corona discharge source (a high voltage source configured to emit corona discharge) and/or an electrospray device (device configured to project charged particles). In some embodiments, the charge source 54 may be configured to generate charge by tribocharging (e.g., friction, etc.), for example by flowing particulate and/or liquid in contact with the dielectric layer 14. The fluid (i.e., the particulate and/or liquid) may be electrically charged and/or include electrically charged components. The fluid may be electrically insulating and/or include electrically insulating components.

The system 10 includes an initiation electrode 30 positioned and configured to initiate a propagating brush discharge at the first surface 16 of the dielectric layer 14. The initiation electrode 30 has a conductive element 32 that has a body 34 and an exposed tip 36.

The exposed tip 36 of the conductive element 32 is positioned and configured for electrical contact with the first surface 16 of the dielectric layer 14. The exposed tip 36 is positioned adjacent to the first surface 16 of the dielectric layer 14, i.e., close enough to the first surface 16 of the dielectric layer 14 to make electrical contact with the first surface 16 during testing as described herein. The exposed tip 36 may be in mechanical contact with the first surface 16 or spaced away from the first surface 16. The distance between the exposed tip 36 and the first surface 16 is small enough that the gap between the exposed tip 36 and the first surface 16 will permit an electrical arc at the testing voltage of the first surface 16 when the exposed tip 36 is at ground potential (or when the voltage differential between the exposed tip 36 and the first surface 16 is less than the testing voltage, e.g., less than 50 kV, less than 20 kV, less than 10 kV, or less than 5 kV). For configurations in which a medium such as air fills the gap between the exposed tip 36 and the first surface 16, the gap distance is small enough to cause dielectric breakdown in the medium. For example, air under standard conditions has a dielectric strength of about 3 kV/mm. For a test voltage of 10 kV at the first surface 16, the exposed tip 36 may be separated from the first surface 16 by an air gap of at most about 3 mm (10 kV divided by 3 mm is greater than 3 kV/mm). Examples of suitable distances between the exposed tip 36 and the first surface 16 include at most 10 mm, at most 5 mm, at most 3 mm, or at most 1 mm.

The exposed tip 36 is relatively small to facilitate optical access to the first surface 16 and/or to promote electrical contact with the first surface 16 at a point. A small exposed tip 36 will obscure less of the first surface 16 than a large exposed tip 36 when observing a propagating brush discharge at the first surface 16 centered at the exposed tip 36. Electrical field strength at the exposed tip 36 and, hence, the propensity for dielectric breakdown and/or electrical discharge is enhanced by a small exposed tip 36 as compared to a large exposed tip 36. Suitable sizes of the exposed tip 36 include a cross sectional area with an effective diameter of less than 3 mm, less than 1 mm and/or greater than 0.05 mm.

The body 34 of the conductive element 32 is electrically isolated from the dielectric layer 14 and the first surface 16. Though the body 34 is electrically isolated from the first surface 16, the body 34 is in electrical communication with the first surface 16 via the exposed tip 36. Electrical current flow between the first surface 16 and the body 34 passes through the exposed tip 36.

The body 34 is isolated from the dielectric layer 14 by spacing the body away from the first surface 16 such that a medium (vacuum, gas, or insulating material) separates the body 34 from the first surface 16. The initiation electrode 30 may include an insulating sheath 38 along the body 34. The body 34 is spaced away from the first surface 16 at a distance such that the separating medium (including the material of the optional insulating sheath 38) may support a high electrical potential without dielectric breakdown or electrical discharge. The high electrical potential is a high voltage suitable for a propagating brush discharge as discussed herein. Some high dielectric strength materials (e.g., fluoropolymers) have a dielectric strength of greater than 50 kV/mm. Suitable spacings between the first surface 16 and the body 34 include at least 2 mm, at least 4 mm, at least 8 mm, or at least 12 mm for an uninsulated body 34 (no insulating sheath 38 or other solid dielectric material between the body 34 and the first surface 16). With intervening solid dielectric materials, suitable spacings between the first surface 16 and the body 34 include at least 1 mm, at least 2 mm, at least 4 mm, or at least 8 mm. Regardless of intervening solid dielectric materials (such as the insulating sheath 38), the initiation electrode 30 along the body 34 typically is spaced away from the first surface 16 by an air, gas, or vacuum gap (e.g., a 1 mm or greater gap) to avoid charge transfer directly from the first surface 16.

Figure 3:
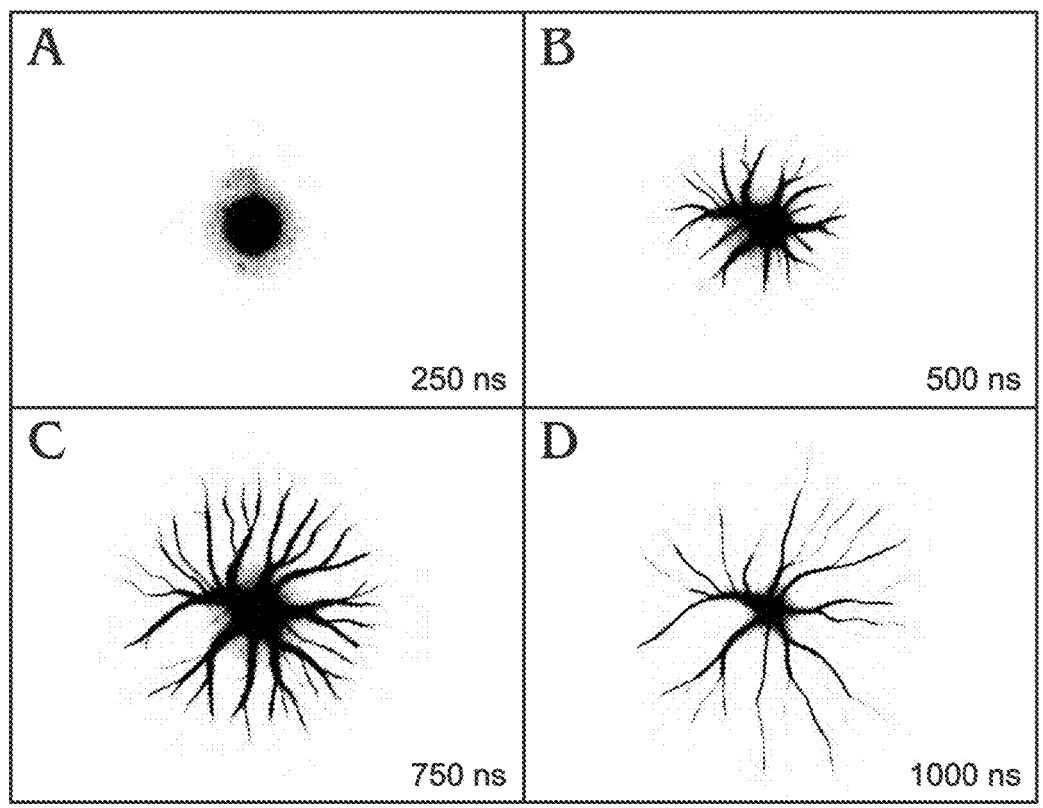
FIG. 3 is an example of propagating brush discharge time evolution. Each of panels A-D represents an image of a propagating brush discharge at different points in time.

The initiation electrode 30 is relatively thin to facilitate optical access to the first surface 16 such that imaging of a propagating brush discharge at the first surface 16 is not significantly obscured by the initiation electrode 30. As illustrated in the examples of FIG. 3, propagating brush discharges have a branch structure with many narrow branches. The height of each of the panels in FIG. 3 corresponds to about 160 mm. Suitable sizes of the initiation electrode 30 include sizes smaller that the width of typical branches of a propagating brush discharge. For example, the cross sectional area of the initiation electrode 30 along the body 34 of the conductive element 32 (including any optional insulating sheath 38) may have an effective diameter of at most 3 mm or at most 1 mm, and generally at least 0.1 mm.

An example of the initiation electrode 30 is an insulated wire with an exposed tip 36. An example of the conductive element 32 is a wire and may be a small gauge wire such as a wire with 20-40 AWG (American Wire Gauge).

As used herein, the effective diameter of an object refers to the diameter of a circle with the same area as the object. For example, the cross sectional area of an electrode may have an effective diameter of a given value. A circle of the given value effective diameter has the same area as the cross sectional area of the electrode. Reference to an effective diameter of an object does not require the object to be circular.

The system 10 includes a high-voltage switch 40 connected to the initiation electrode 30 and configured to selectively isolate the conductive element 32 of the initiation electrode 30 from ground potential. The high-voltage switch 40 may include and/or may be one or more of a high-voltage relay, a high-voltage reed relay, and a high-voltage solid-state relay. The high-voltage switch 40 is configured to isolate a voltage of at least 5 kV or at least 20 kV, and generally less than 100 kV. The high-voltage switch 40 is electrically connected to the conductive element 32 and to ground potential at different contacts. Typically, the high-voltage switch 40 is a single-pole, single-throw type with one pole connected to the conductive element 32 and the other pole connected to ground. The electrical connection to the high-voltage switch 40 may be direct or indirect. In particular and as discussed further herein, a current sensor 56 may be inserted in series between the conductive element 32 and the high-voltage switch 40 and/or in series between the high-voltage switch 40 and ground. When the high-voltage switch 40 is activated, the high-voltage switch 40 makes electrical contact between the conductive element 32 and ground potential. When the high-voltage switch 40 is deactivated, the high-voltage switch 40 breaks electrical contact between the conductive element 32 and ground potential. Hence, the high-voltage switch 40 may selectively isolate the conductive element 32 from ground potential when the conductive element has an electrical potential magnitude of at least 5 kV or at least 20 kV. Activation and/or deactivation of the high-voltage switch 40 do not necessarily require application of external energy. The high-voltage switch 40 may be stable in either or both of the activated and deactivated states without application of external energy.

Typically, the high-voltage switch 40 is configured to switch to the activated state relatively rapidly, e.g., within a few milliseconds of being commanded to switch. Switching rapidly may provide a reproducible initiation time for propagating brush discharges, especially as compared to traditional techniques of triggering a propagating brush discharge in which a grounded electrode is brought to a charged surface. By electrically connecting the conductive element 32 to ground potential while the conductive element 32 is adjacent to the first surface 16, one may avoid complications and experimental artifacts due to partial unintended discharge that may occur with moving electrodes (as used in traditional methods, small corona or streamer currents may form between the moving electrode and the dielectric surface before the tip may initiate the propagating brush discharge).

As used herein, electrical isolation with respect to high voltage components refers to a leakage current between the electrical components of less than 1 μA (microampere) when the high voltage is applied. Alternatively expressed, electrical isolation may refer to an electrical resistance between the components of greater than 1 GΩ (gigaohm) per 1 kV applied between the components. A high voltage is a voltage magnitude of greater than 1 kV, unless otherwise specified.

The system 10 may include an optical sensor 44 positioned and configured to sense light generated at the first surface 16 of the dielectric layer 14 due to a propagating brush discharge centered at the exposed tip 36 of the initiation electrode 30. The propagating brush discharge being centered at the exposed tip 36 of the initiation electrode 30 indicates that the central point of the Lichtenberg figure of the propagating brush discharge is at the point where the exposed tip 36 makes electrical contact with the first surface 16. The central point of the Lichtenberg figure is where the branches of the figure radiate from and is not necessarily the geometric center of the figure. Electrical charge (typically in the form of electrons) may flow to or from the central point of the figure.

The optical sensor 44 is configured to sense the intensity of light and may be configured to spatially resolve and/or temporally resolve the light from a propagating brush discharge. For example, the optical sensor 44 may be a camera or other two-dimensional imager that is configured to record the intensity and spatial distribution of light at the first surface 16. As another example, the optical sensor 44 may be a camera that is configured to collect a sequence of image frames.

Figure 2:
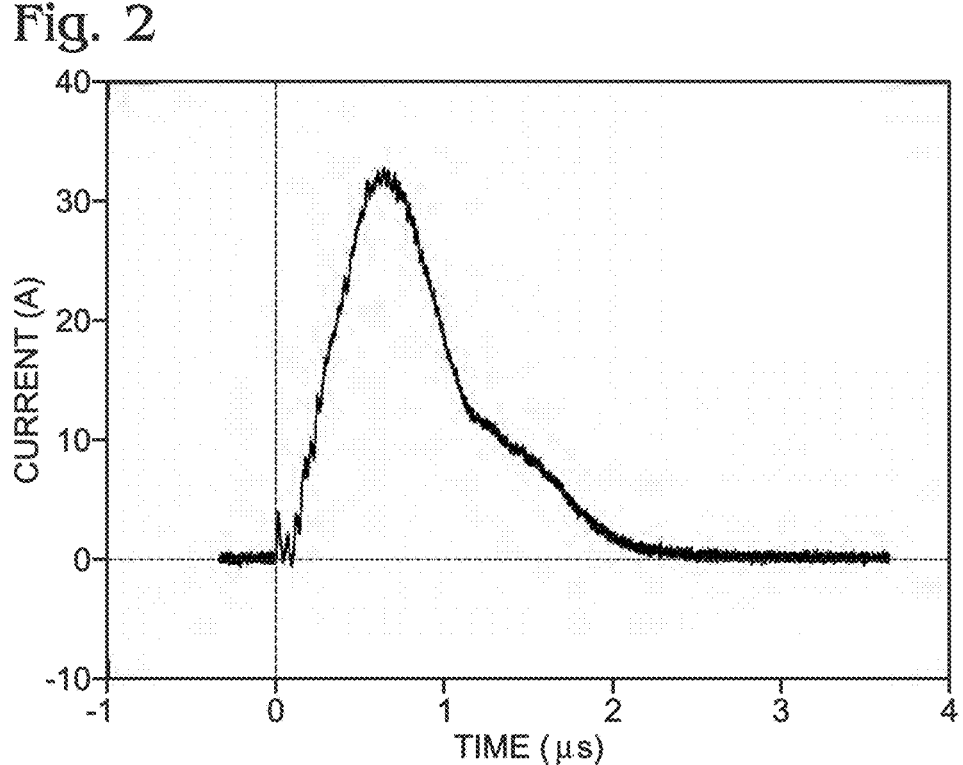
FIG. 2 is an example current trace measured by an electrode recording a propagating brush discharge.

A propagating brush discharge is a relatively rapid phenomenon. As shown in the example of FIG. 2, the total electrical current for a propagating brush discharge may occur in a few microseconds. FIG. 2 is the total electrical current of a propagating brush discharge recorded as a function of time. The propagating brush discharge begins at about the time marker at 0 μs. The total electrical current increases to a peak of about 30 A near 1 μs and has a tail that extends beyond 2 μs in this example. System 10 may include a current sensor 56 configured to measure the total electrical current of a propagating brush discharge at the first surface 16 (as a function of time (e.g., instantaneous total electrical current), integrated over a predefined interval (e.g., discharged charge), and/or integrated over the period of the propagating brush discharge (e.g., total discharged charge)). The current sensor 56 also may be referred to as a charge sensor and/or a discharge measuring device. The current sensor 56 may include and/or may be a capacitor (or other current integrating device) configured to collect charge from the discharged current flowing in the conductive element 32 of the initiation electrode 30, an inductive current meter configured to measure current flowing in the conductive element 32 of the initiation electrode 30, and/or an ammeter in series with the conductive element 32 of the initiation electrode 30. An inductive current meter may be electrically isolated from the high voltages that may be achieved at the first surface 16 and in the initiation electrode 30. An inductive current meter may include and/or may be a current clamp, a current transformer, and/or a Rogowski coil. Additionally or alternatively, current sensor 56 may include a rapid response element such as a current transformer that may indicate the initiation of a propagating brush discharge and additionally may be used to trigger other sensing devices (in the current sensor 56 and/or in the system 10).

In the example where the current sensor 56 includes a capacitor or other current integrating device, the device generally is arranged in series with the current path through the conductive element 32 and the high-voltage switch 40 to ground. For example, a capacitor may be connected between one contact of the high-voltage switch 40 and ground. When the high-voltage switch 40 is switched to connect the conductive element 32 to ground, the charge from the propagating brush discharge will flow to and accumulate in the capacitor. The ungrounded terminal of the capacitor will achieve a voltage according to the capacitance of the capacitor (the voltage is the product of the accumulated charge and the capacitance). The capacitance of the capacitor may be selected to produce a voltage in response to a propagating brush discharge that is substantially less than the high voltage of the propagating brush discharge. For example, the capacitance may be at least 0.1 microfarad. The current sensor 56 may also include a voltmeter to measure the voltage induced in the current integrating device by the propagating brush discharge.

In some circumstances, a propagating brush discharge may last over 10 μs. Generally, the light emitted from a propagating brush discharge is emitted during the time of significant electrical current. Hence, a propagating brush discharge may emit light for at least 2 μs or at least 10 μs, and generally less than 1,000 μs.

The optical sensor 44 may be configured to sense light from the first surface 16 during the entire time of a propagating brush discharge or during a portion of the time of a propagating brush discharge. For example, the optical sensor 44 may be configured to collect light during an exposure time of at least 10 μs or at least 1,000 μs, and optionally less than 100 s (seconds). As another example, the optical sensor 44 may be configured to collect light during an exposure time of at most 1 μs, at most 0.3 μs, or at most 0.1 μs. For long exposure times (e.g., 10 μs or more), the optical sensor 44 may be configured to be exposed long enough to accommodate delays in activating the high-voltage switch 40. The high-voltage switch 40 may actually connect the conductive element 32 of the initiation electrode 30 to ground potential several milliseconds after being commanded to do so. Hence, the optical sensor 44 may be configured to collect light during the delay time and during the time of the ensuing propagating brush discharge.

The optical sensor 44 is positioned and configured to sense light from an observed region 46 of the first surface 16. The observed region 46 generally is similar in size to (and/or at least as large as) an expected propagating brush discharge. A propagating brush discharge may have a spatial extent with an effective diameter that is at least 50 mm, at least 100 mm, or at least 200 mm. For example, heights of the panels in FIG. 3 correspond to about 160 mm. Hence, the observed region 46 on the first surface 16 may have an effective diameter that is at least 50 mm, at least 100 mm, or at least 200 mm, and generally at most 10 m (meters). The observed region 46 may encompass substantially all of the propagating brush discharge or a portion of the propagating brush discharge. The observed region 46 may not be centered on the exposed tip 36 and may not include the exposed tip 36.

The optical sensor 44 may be configured to produce temporally resolved images of the light emitted by the propagating brush discharge. For example, the optical sensor 44 may be a high-speed camera configured to image a propagating brush discharge with a frame rate of at least 0.5 MFPS (million frames per second), at least 1 MFPS, at least 4 MFPS, or at least 10 MFPS (corresponding to frame exposure times of about at most 2 μs, at most 1 μs, at most 0.25 μs, or at most 0.1 μs).

FIG. 3 illustrates four images of the propagating brush discharge characterized in FIG. 2. The four images were collected at different points in time with a high-speed camera. Each of the four panels has the same scale and the heights of the panels correspond to about 160 mm. In panel A, the propagating brush discharge has been triggered 250 ns (nanoseconds) prior (250 ns is 0.25 μs). The character of the initial emission is that of a corona-like discharge, generally symmetrical with a smooth central peak and no distinct branching structure. In panel B, 500 ns after the trigger, the propagating brush discharge has evolved to form short branches in a Lichtenberg form. In panel C, 750 ns after the trigger, the propagating brush discharge has grown in spatial extent and developed a complex branch structure. In panel D, 1,000 ns after the trigger, the propagating brush discharge has fewer defined branches than in panel C. Some of the branches have continued to grow and some have disappeared relative to panel C. Panel C has the peak integrated brightness of the panels and is the image closest to the total electrical current peak of the propagating brush discharge. With a temporally resolved, imaging optical sensor 44 (such as a high-speed camera), the temporal evolution of individual branches may be analyzed.

Returning to FIG. 1, system 10 may include a flammable gas 60 at the first surface 16 of the dielectric layer 14 where the propagating brush discharge may be formed. If a propagating brush discharge is formed by grounding the initiation electrode 30, the flammable gas 60 will ignite and indicate the formation of the propagating brush discharge. If no propagating brush discharge is formed (e.g., grounding the initiation electrode 30 produces a corona-like discharge or no discharge), the flammable gas 60 will not ignite. The ignition of the flammable gas 60 may be indicated by an ignition detector 62. The ignition detector 62 may include, and/or may be, the optical sensor 44, a flame sensor, an ion sensor, a pressure sensor, a temperature sensor, and/or a microphone. Additionally or alternatively, the ignition detector 62 may include, and/or may be, a conformable element such as a burst diaphragm that may rupture, unseal, deform, burn, and/or melt in response to ignition of the flammable gas 60. Ignition of the flammable gas 60 may be quenched in certain regions near surfaces that provide sufficient thermal quenching of the flame front. Typical quenching distances are about 1-2 mm. Thin and/or small initiation electrode 30 dimensions and suitable placement may reduce the effects of thermal quenching due to the initiation electrode 30. For example, the disclosed values for the cross sectional area of the exposed tip 36, the cross sectional area of the initiation electrode 30 along the body 34, the wire gauge of the initiation electrode 30, and the spacing between the first surface 16 and the body 34 may be suitable to reduce the effects of thermal quenching.

System 10 may include a controller 50 to operate aspects of the system 10 such as the high-voltage switch 40, the optical sensor 44, the charge source 54 and/or the current sensor 56. The controller 50 may be programmed and/or configured to perform any of the methods described herein. The controller 50 is programmed and/or configured to operate the high-voltage switch 40 to electrically ground the initiation electrode 30 (more specifically to electrically ground the conductive element 32 of the initiation electrode 30). Additionally, the controller 50 is programmed and/or configured to operate the optical sensor to collect light from the first surface 16 of the dielectric layer 14 due to a propagating brush discharge. Generally, the controller 50 is programmed and/or configured to coordinate the electrical grounding (which may initiate a propagating brush discharge) and the light collection such that the light collection is performed at a time that would include the propagating brush discharge triggered by the electrical grounding. For example, the controller 50 may be programmed and/or configured to cause the high-voltage switch 40 to ground the initiation electrode 30 and the optical sensor 44 to collect light within 10 μs of electrically grounding the initiation electrode. The high-voltage switch 40 may not switch as soon as commanded by the controller 50. For example, some high-voltage reed relays may switch 5-10 ms after being commanded to switch. Hence, the controller 50 may be programmed and/or configured to compensate for known delays and/or jitter in the response time of the high-voltage switch 40 and/or the optical sensor 44.

Figure 4:
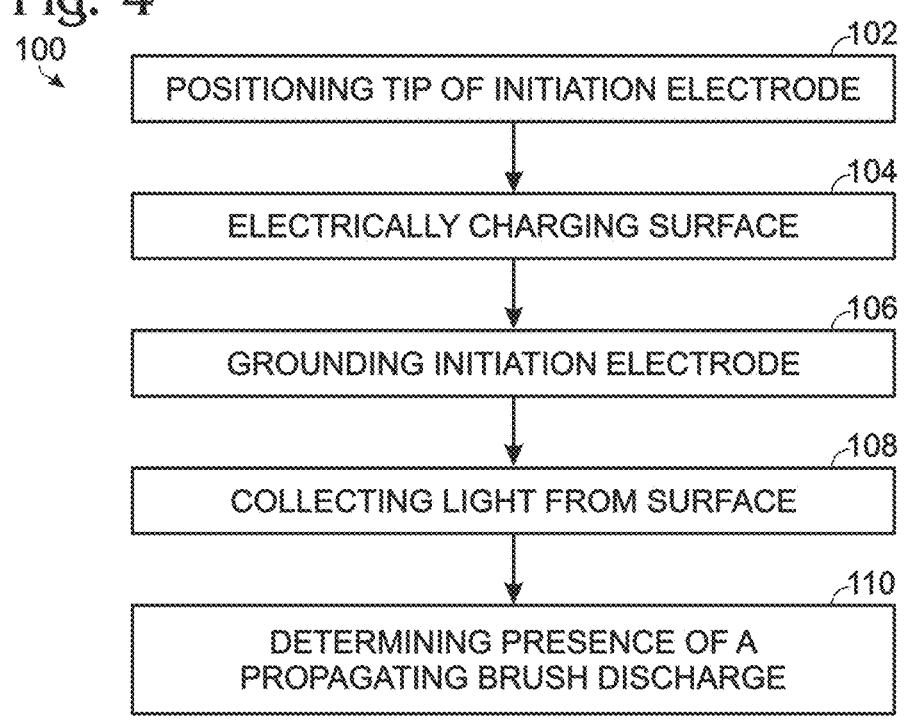
FIG. 4 is a schematic representation of methods of performing a propagating brush discharge test according to the present disclosure.

FIG. 4 schematically represents methods 100 of performing a propagating brush discharge test. Methods 100 include positioning 102 an exposed tip (such as exposed tip 36) of an initiation electrode (such as initiation electrode 30) in close proximity (i.e., adjacent) to a first surface (such as first surface 16) of a dielectric layer (such as dielectric layer 14). The dielectric layer is backed by a grounded layer (such as grounded layer 20) opposite the first surface of the dielectric layer. That is, the grounded layer is in mechanical and electrical contact with a second surface (such as second surface 18) of the dielectric layer that is opposite the first surface. Close proximity of the exposed tip of the initiation electrode to the first surface is a position in which the exposed tip can make electrical contact with the first surface when the first surface is charged to a high voltage such as a high voltage of a propagating brush discharge and the exposed tip is grounded (at ground potential). Generally, the exposed tip is positioned such that a voltage differential between the exposed tip and the first surface of less than 50 kV is sufficient to cause an electrical contact between the exposed tip and the first surface. For example, positioning 102 may include positioning the exposed tip to a location as described with respect to exposed tip 36 and first surface 16, e.g., within 10 mm, within 5 mm, within 3 mm, within 1 mm, or in mechanical contact. Positioning 102 may include positioning and/or arranging a body of the initiation electrode in electrical isolation from the first surface, for example as described with respect to the location of the initiation electrode 30 along the body 34 of the conductive element 32 relative to the first surface 16.

Methods 100 include electrically charging 104 the first surface of the dielectric layer after positioning 102. Generally, the initiation electrode is not moved during electrically charging 104 (i.e., the position of the initiation electrode after positioning 102 is substantially maintained). Electrically charging 104 is performed while the grounded layer is at ground potential and while the initiation electrode is isolated from ground potential. Methods 100 may include grounding the grounded electrode and/or electrically isolating the initiation electrode from ground potential simultaneously with or prior to the electrically charging 104. Electrically isolating the initiation electrode may include isolating the initiation electrode from ground potential with a high-voltage switch (such as high-voltage switch 40). Typically, the initiation electrode is not connected to any voltage source or ground while electrically charging 104 the first surface of the dielectric layer. Hence, the initiation electrode may float to the potential of the first surface as it is charged.

Electrically charging 104 includes charging the first surface to an electrical potential suitable for a propagating brush discharge (e.g., a voltage with a magnitude of at least 4 kV, at least 8 kV, or at least 16 kV, and generally at most 100 kV, relative to ground potential). Electrically charging 104 may include applying charge to the first surface with a charge source (such as charge source 54). For example, electrically charging 104 may include using a corona discharge source to deposit electrical charge onto the first surface.

After electrically charging 104, methods 100 include grounding 106 the initiation electrode, i.e., electrically connecting the initiation electrode to ground potential. Grounding 106 the initiation electrode is grounding the conductive body of the initiation electrode, i.e., electrically connecting the initiation electrode to ground potential. Grounding 106 is performed while the initiation electrode is substantially at the final position after positioning 102 and electrically charging 104. The exposed tip of the initiation electrode is adjacent to the first surface during electrically charging 104, before grounding 106, and during grounding 106.

Grounding 106 the initiation electrode connects the exposed tip of the initiation electrode (adjacent to the first surface) to ground potential. If the dielectric layer has a bi-layer of opposite charge on the first surface and the second surface with a sufficient voltage difference, the grounding 106 of the initiation electrode may initiate a propagating brush discharge. While the initiation electrode is connected to ground, the charge accumulated on (at least some portion of) the first surface (via the electrically charging 104) may be neutralized (partially or completely) by charge supplied by the exposed tip. For example, excess charge on the first surface may flow to/from ground potential through the exposed tip and the initiation electrode. Simultaneously, electrical current will flow in the grounded layer that will be of an equal magnitude but opposite in polarity.

Grounding 106 the initiation electrode may include operating a high-voltage switch (such as high-voltage switch 40) used to electrically isolate the initiation electrode. Using the high-voltage switch to ground the initiation electrode may rapidly switch the voltage of the initiation electrode from the electrical potential of the first surface to ground potential. Using the high-voltage switch may provide a reproducible initiation time for the propagating brush discharge, especially as compared to traditional methods.

In traditional methods of triggering a propagating brush discharge, a grounded initiation electrode is brought to a charged surface. The grounded initiation electrode causes a propagating brush discharge at a relatively uncontrolled time associated with the particulars of approach speed, electrode shape, electrode position, dielectric layer material, voltage of the charged surface, and/or other situation-specific parameters. In contrast, methods 100 initiate a propagating brush discharge within a relatively limited period of time that is within the control of the one performing the methods 100. By electrically charging 104 the first surface in the presence of an initiation electrode that is isolated from ground and then grounding 106 the initiation electrode, parameters such as approach speed, electrode shape, electrode position, dielectric layer material, and voltage of the charged surface do not significantly affect the time when the propagating brush discharge is triggered or are entirely inapplicable (such as approach speed). With the approach of methods 100, the period of time in which the propagating brush discharge is triggered is substantially defined by the time when grounding 106 is performed and the speed and reliability of devices used to switch the initiation electrode to ground potential (such as the high-voltage switch). Methods 100 may initiate a propagating brush discharge within a time period that is reliably less than 100 ms, less than 10 ms, less than 1 ms, less than 100 µs, or less than 10 µs.

Methods 100 may include collecting light 108 from a region that includes the first surface of the dielectric layer and the exposed tip of the initiation electrode. Collecting light 108 may include collecting light generated at the first surface of the dielectric layer due to a propagating brush discharge centered at the exposed tip of the initiation electrode and/or collecting light from ignition of a flammable gas (such as flammable gas 60) introduced to the first surface before grounding 106.

Collecting light 108 may include using an optical sensor (such as optical sensor 44) and may include collecting temporally and/or spatially resolved data. Additionally or alternatively, methods 100 may include detecting ignition of the flammable gas by techniques other than collecting light, such as using a flame sensor, an ion sensor, a pressure sensor, a temperature sensor, a microphone, and/or a conformable element as discussed herein.

Because a propagating brush discharge may only exist and emit light for a few microseconds after initiation, collecting light 108 is performed proximate in time with grounding 106 the initiation electrode and initiating the potential propagating brush discharge. Generally, collecting light 108 is performed to collect light from the first surface within 10 µs after grounding 106 so that light emitted by the propagating brush discharge (if any propagating brush discharge occurs) is collected. Collecting light 108 may be performed concurrently with grounding 106. Collecting light 108 may begin before, during, or after grounding 106. Collecting light 108 typically ends after grounding 106 (e.g., after a typical discharge time for a propagating brush discharge has elapsed). Collecting light 108 may include imaging (spatially resolved light collection) the first surface within 10 µs of grounding 106. Collecting light 108 may include collecting light (e.g., imaging) during an exposure time of at least 10 µs or at least 1,000 µs, and optionally less than 100 s. In alternate, collecting light 108 may include collecting light (e.g., imaging) during an exposure time of at most 1 µs, at most 0.3 µs, or at most 0.1 µs. For long exposure times (e.g., 10 µs or more), the exposure time may be selected to accommodate delays in operating devices associated with grounding 106 (e.g., the high-voltage switch). For shorter exposure times, collecting light 108 may include collecting a sequence of light samples (e.g., image frames). The sequence of light samples may include a sequence of samples of the light emitted by the propagating brush discharge (if any occurs). Collecting light 108 may include using a high-speed camera to collect spatially-resolved images from the first surface of the propagating brush discharge in a sequence of image frames with a frame rate of at least 0.5 MFPS, at least 1 MFPS, at least 4 MFPS, or at least 10 MFPS (corresponding to frame exposure times of about at most 2 µs, at most 1 µs, at most 0.25 µs, or at most 0.1 µs).

Methods 100 may include determining 110 the presence of a propagating brush discharge after grounding 106 the initiation electrode. If grounding 106 the initiation electrode triggers a propagating brush discharge, the propagating brush discharge may be detected by the light and/or the electrical current generated by the propagating brush discharge. For example, light from the propagating brush discharge may be detected by collecting light 108 from the first surface. As another example, the electrical current generated by the propagating brush discharge may be detected by monitoring the electrical current flowing in the initiation electrode after grounding 106 the initiation electrode (i.e., monitoring electrical current flowing to/from the initiation electrode to ground potential). As described herein, electrical current flowing in the initiation electrode may be monitored with a current sensor such as current sensor 56.

The presence of a propagating brush discharge may be determined according to the magnitude, temporal structure, or spatial structure of the detected light, electrical current, or related quantities. The presence of a propagating brush discharge may be confirmed if the magnitude of collected light exceeds a brightness threshold or if the magnitude of detected electrical current exceeds a peak current threshold. The presence of a propagating brush discharge may be confirmed by comparing the onset time, duration, and/or decay time of collected light or detected electrical current to corresponding expected values for propagating brush discharges. Additionally or alternatively, spatial characteristics of the collected light (such as the number of branches, the length of branches, and/or the number of branching points) may be used to determine the presence of a propagating brush discharge. For example, a relatively small and/or symmetric discharge may be classified as a corona discharge (or a corona-like discharge) while a larger and/or complexly branched discharge may be classified as a propagating brush discharge.

Examples of inventive subject matter according to the present disclosure are described in the following enumerated paragraphs.

A1. A system for performing a propagating brush discharge test, the system comprising:
 a grounded layer;
 a dielectric layer that has a first surface and is backed by the grounded layer opposite the first surface of the dielectric layer;
 an initiation electrode with a conductive element that has a body and an exposed tip, wherein the exposed tip is positioned adjacent to the first surface of the dielectric layer such that a voltage differential between the exposed tip and the first surface of less than 50 kV is sufficient to cause an electrical contact between the exposed tip and the first surface, wherein the body of the conductive element is electrically isolated from the dielectric layer;
 a high-voltage switch connected to the initiation electrode and configured to selectively isolate the conductive element of the initiation electrode from ground potential;
 a sensor positioned and configured to detect a propagating brush discharge centered at the exposed tip of the initiation electrode; and
 a controller programmed to operate the high-voltage switch to electrically ground the initiation electrode.

A1.1. The system of paragraph A1, wherein the sensor is an optical sensor positioned and configured to sense light generated due to the propagating brush discharge.

A1.1.1. The system of paragraph A1.1, wherein the optical sensor is positioned and configured to sense light generated at the first surface of the dielectric layer due to the propagating brush discharge.

A1.1.2. The system of any of paragraphs A1.1-A1.1.1, wherein the optical sensor is positioned and configured to detect light generated by ignition of a flammable gas in contact with the first surface.

A1.1.3. The system of any of paragraphs A1.1-A1.1.2, wherein the controller is programmed to operate the optical sensor to collect light from the propagating brush discharge.

A1.2. The system of any of paragraphs A1-A1.1.3, wherein the sensor is configured to detect ignition of a flammable gas in contact with the first surface that is ignited due to the propagating brush discharge.

A1.2.1. The system of paragraph A1.2, wherein the sensor includes, optionally is, at least one of a flame sensor, an ion sensor, a pressure sensor, a temperature sensor, a microphone, a burst diaphragm, or a conformable element.

A1.3. The system of any of paragraphs A1-A1.2.1, further comprising a flammable gas in contact with the first surface of the dielectric layer.

A2. The system of any of paragraphs A1-A1.3, wherein the initiation electrode includes an insulating sheath along the body of the conductive element.

A2.1. The system of paragraph A2, wherein the insulating sheath of the initiation electrode is spaced apart from the first surface of the dielectric layer.

A3. The system of any of paragraphs A1-A2.1, wherein the body of the initiation electrode is spaced apart from the first surface of the dielectric layer by at least 4 mm.

A4. The system of any of paragraphs A1-A3, wherein the exposed tip of the initiation electrode is within 10 mm or within 3 mm of the first surface of the dielectric layer.

A5. The system of any of paragraphs A1-A4, wherein the exposed tip of the initiation electrode contacts the first surface of the dielectric layer.

A6. The system of any of paragraphs A1-A5, wherein the initiation electrode is an insulated wire.

A7. The system of any of paragraphs A1-A6, wherein the conductive element is a wire.

A8. The system of any of paragraphs A1-A7, wherein a cross sectional area of the exposed tip has an effective diameter of less than 1 mm, and optionally greater than 0.05 mm.

A9. The system of any of paragraphs A1-A8, wherein a cross sectional area of the initiation electrode along the body of the conductive element has an effective diameter of at most 3 mm or at most 1 mm.

A10. The system of any of paragraphs A1-A9, wherein the high-voltage switch is one or more of a high-voltage relay, a high-voltage reed relay, and a high-voltage solid-state relay.

A11. The system of any of paragraphs A1-A10, wherein the high-voltage switch is configured to isolate a voltage of at least 5 kV or at least 20 kV.

A12. The system of any of paragraphs A1-A11, wherein the high-voltage switch is configured to selectively isolate the conductive element of the initiation electrode from ground potential at a voltage magnitude of the conductive element of at least 5 kV or at least 20 kV, relative to ground potential.

A13. The system of any of paragraphs A1.1-A12, when dependent from paragraph A1.1, wherein the optical sensor is a camera.

A13.1. The system of paragraph A13, wherein the camera is configured to image the first surface of the dielectric layer with an exposure time of at least 10 µs, and optionally less than 100 s.

A13.2. The system of paragraph A13, wherein the camera is configured to image the first surface of the dielectric layer with an exposure time of at most 1 µs, at most 0.3 µs, or at most 0.1 µs.

A13.3. The system of any of paragraphs A13-A13.2, wherein the camera is configured to image the first surface of the dielectric layer with a sequence of image frames.

A14. The system of any of paragraphs A1-A13.3, wherein the first surface of the dielectric layer has a voltage with a magnitude of at least 4 kV, at least 8 kV, at least 16 kV, and optionally at most 100 kV, relative to ground potential.

A15. The system of any of paragraphs A1-A14, further comprising a charge source configured to charge the first surface of the dielectric layer to a voltage with a magnitude of at least 4 kV, at least 8 kV, at least 16 kV, and optionally at most 100 kV, relative to ground potential.

A15.1. The system of paragraph A15, wherein the charge source is a corona discharge source.

A15.2. The system of paragraph A15, wherein the charge source is a source of fluid that is configured to flow across the first surface.

B1. A method for performing a propagating brush discharge test on a dielectric layer, the method comprising:
positioning an exposed tip of an initiation electrode adjacent to a first surface of the dielectric layer, wherein the dielectric layer is backed by a grounded layer opposite the first surface of the dielectric layer;
after positioning, electrically charging the first surface of the dielectric layer to a voltage with a magnitude of at least 4 kV relative to ground potential, while the grounded layer is at ground potential and the initiation electrode is isolated from ground potential; and
after electrically charging, electrically connecting the initiation electrode to ground potential so that the exposed tip of the initiation electrode neutralizes charge on the first surface of the dielectric layer.

B2. The method of paragraph B1, further comprising collecting light from a region that includes the first surface of the dielectric layer and the exposed tip of the initiation electrode.

B2.1. The method of paragraph B2, wherein collecting light includes collecting light generated at the first surface of the dielectric layer due to a propagating brush discharge centered at the exposed tip of the initiation electrode.

B2.2. The method of any of paragraphs B2-B2.1, wherein collecting light includes imaging the first surface within 10 µs of electrically connecting the initiation electrode to ground potential.

B2.3. The method of any of paragraphs B2-B2.2, wherein collecting light includes imaging the first surface with an exposure time of at least 10 µs or at least 1,000 µs, and optionally less than 100 s.

B2.4. The method of any of paragraphs B2-B2.2, wherein collecting light includes imaging the first surface with an exposure time of at most 1 µs, at most 0.3 µs, or at most 0.1 µs.

B2.5. The method of any of paragraphs B2-B2.4, wherein collecting light includes imaging the first surface with a sequence of image frames.

B2.6. The method of any of paragraphs B2-B2.5, wherein collecting light includes acquiring an image of the first surface and the method further comprises determining a presence of a propagating brush discharge at the first surface based upon the image of the first surface.

B3. The method of any of paragraphs B1-B2.6, wherein positioning the exposed tip of the initiation electrode includes spacing a body of the initiation electrode apart from the first surface of the dielectric layer by at least 1 mm.

B4. The method of any of paragraphs B1-B3, wherein positioning the exposed tip includes positioning the exposed tip within 10 mm or within 3 mm of the first surface of the dielectric layer.

B5. The method of any of paragraphs B1-B4, wherein positioning the exposed tip includes contacting the exposed tip to the first surface of the dielectric layer.

B6. The method of any of paragraphs B1-B5, further comprising electrically isolating the initiation electrode from ground potential with a high-voltage switch.

B6.1. The method of paragraph B6, wherein the electrically connecting the initiation electrode to ground potential includes operating the high-voltage switch.

B7. The method of any of paragraphs B1-B6.1, wherein the electrically connecting the initiation electrode to ground potential initiates a propagating brush discharge to neutralize charge on the first surface of the dielectric layer.

B8. The method of any of paragraphs B1-B7, wherein after the electrically charging, the magnitude of the voltage of the first surface of the dielectric layer is at least 8 kV or at least 16 kV, and optionally at most 100 kV, relative to ground potential.

B9. The method of any of paragraphs B1-B8, wherein electrically charging the first surface includes charging the first surface with at least one of a corona source and a charged fluid.

B10. The method of any of paragraphs B1-B9, further comprising determining a presence of a propagating brush discharge after grounding the initiation electrode based upon an electrical current in the initiation electrode.

B11. The method of any of paragraphs B1-B10, further comprising introducing a flammable gas to the first surface before electrically connecting the initiation electrode to ground potential.

B11.1. The method of paragraph B11, further comprising detecting ignition of the flammable gas in response to electrically connecting the initiation electrode to ground potential.

B12. The method of any of paragraphs B1-B11.1, wherein the dielectric layer, the grounded layer, the initiation electrode, and/or the high-voltage switch is the respective dielectric layer, grounded layer, initiation electrode and/or high-voltage switch of any of paragraphs A1-A15.2.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entities in the list of entities, and is not limited to at least one of each and every entity specifically listed within the list of entities. For example, "at least one of A and B" (or, equivalently, "at least one of A or B," or, equivalently, "at least one of A and/or B") may refer to A alone, B alone, or the combination of A and B.

As used herein, the singular forms "a", "an" and "the" may be intended to include the plural forms as well, unless the context clearly indicates otherwise.

The various disclosed elements of systems and steps of methods disclosed herein are not required of all systems and methods according to the present disclosure, and the present disclosure includes all novel and non-obvious combinations and subcombinations of the various elements and steps disclosed herein. Moreover, any of the various elements and steps, or any combination of the various elements and/or steps, disclosed herein may define independent inventive subject matter that is separate and apart from the whole of a disclosed system or method. Accordingly, such inventive subject matter is not required to be associated with the specific systems and methods that are expressly disclosed herein, and such inventive subject matter may find utility in systems and/or methods that are not expressly disclosed herein.

The invention claimed is:

1. A system for performing a propagating brush discharge test, the system comprising:
    a grounded layer;
    a dielectric layer that has a first surface and is backed by the grounded layer opposite the first surface of the dielectric layer;
    an initiation electrode with a conductive element that has a body and an exposed tip, wherein the exposed tip is positioned adjacent to the first surface of the dielectric layer such that a voltage differential between the exposed tip and the first surface is sufficient to cause an electrical contact between the exposed tip and the first surface, wherein the body of the conductive element is electrically isolated from the dielectric layer;
    a high-voltage switch connected to the initiation electrode and configured to selectively isolate the conductive element of the initiation electrode from ground potential;
    a sensor positioned and configured to detect a propagating brush discharge centered at the exposed tip of the initiation electrode; and
    a controller programmed to operate the high-voltage switch to electrically ground the initiation electrode.

2. The system of claim 1, wherein the sensor is configured to detect ignition of a flammable gas in contact with the first surface that is ignited due to the propagating brush discharge.

3. The system of claim 2, wherein the sensor includes at least one of a flame sensor, an ion sensor, a pressure sensor, a temperature sensor, a microphone, a burst diaphragm, or a conformable element.

4. The system of claim 1, further comprising a flammable gas in contact with the first surface of the dielectric layer.

5. The system of claim 1, wherein the initiation electrode includes an insulating sheath along the body of the conductive element.

6. The system of claim 5, wherein the insulating sheath of the initiation electrode is spaced apart from the first surface of the dielectric layer.

7. The system of claim 1, wherein the body of the initiation electrode is spaced apart from the first surface of the dielectric layer by at least 4 mm.

8. The system of claim 1, wherein the exposed tip of the initiation electrode is within 10 mm of the first surface of the dielectric layer.

9. The system of claim 1, wherein the exposed tip of the initiation electrode contacts the first surface of the dielectric layer.

10. The system of claim 1, wherein the exposed tip is positioned adjacent to the first surface of the dielectric layer such that a voltage differential of less than 50 kV between the exposed tip and the first surface is sufficient to cause the electrical contact between the exposed tip and the first surface.

11. The system of claim 1, wherein a cross sectional area of the exposed tip has an effective diameter of less than 1 mm.

12. The system of claim 1, wherein a cross sectional area of the initiation electrode along the body of the conductive element has an effective diameter of at most 3 mm.

13. The system of claim 1, wherein the high-voltage switch is one or more of a high-voltage relay, a high-voltage reed relay, and a high-voltage solid-state relay.

14. The system of claim 1, wherein the high-voltage switch is configured to isolate a voltage of at least 5 kV.

15. The system of claim 1, wherein the high-voltage switch is configured to selectively isolate the conductive element of the initiation electrode from ground potential at a voltage magnitude of the conductive element of at least 5 kV, relative to ground potential.

16. The system of claim 1, wherein the first surface of the dielectric layer has a voltage with a magnitude of at least 4 kV, relative to ground potential.

17. The system of claim 1, further comprising a charge source configured to charge the first surface of the dielectric layer to a voltage with a magnitude of at least 4 kV, relative to ground potential.

18. The system of claim 17, wherein the charge source is a corona discharge source.

19. The system of claim 17, wherein the charge source is a source of fluid that is configured to flow across the first surface.

20. A system for performing a propagating brush discharge test on a test article, the system comprising:
- an initiation electrode with a conductive element and an insulating sheath along a body of the conductive element, wherein the conductive element has an exposed tip configured to be positioned adjacent to the test article;
- a high-voltage switch connected to the initiation electrode and configured to selectively isolate the conductive element from ground potential;
- an optical sensor positioned and configured to sense light generated at the test article due to a propagating brush discharge centered at the exposed tip of the conductive element; and
- a controller configured to operate the high-voltage switch and the optical sensor to obtain image data of the propagating brush discharge.

* * * * *